US005721365A

United States Patent [19]

Keefer et al.

[11] Patent Number: 5,721,365

[45] Date of Patent: Feb. 24, 1998

[54] N-SUBSTITUTED PIPERAZINE NONOATES

[76] Inventors: Larry Kay Keefer, 7016 River Rd., Bethesda, Md. 20817; Joseph E. Saavedra, 7089 Brown's La., Thurmont, Md. 21788; Joseph Anthony Hrabie, 630 Grant Pl., Frederick, Md. 21702

[21] Appl. No.: 475,732

[22] Filed: Jun. 7, 1995

Related U.S. Application Data

[63] Continuation-in-part of Ser. No. 17,270, Feb. 12, 1993, and Ser. No. 950,637, Sep. 23, 1992, Pat. No. 5,366,997, which is a continuation-in-part of Ser. No. 764,908, Sep. 24, 1991, abandoned, said Ser. No. 17,270, is a division of Ser. No. 743,892, Aug. 12, 1991, Pat. No. 5,208,233, which is a continuation-in-part of Ser. No. 409,552, Sep. 15, 1989, Pat. No. 5,039,705.

[51] Int. Cl.$^6$ .................................................. C07D 241/04
[52] U.S. Cl. .......................... 544/382; 544/358; 544/359; 544/360; 544/390
[58] Field of Search .................................. 544/382, 358, 544/359, 360, 390; 514/255

[56] References Cited

U.S. PATENT DOCUMENTS

| | | | |
|---|---|---|---|
| 2,954,314 | 9/1960 | Metger et al. | 167/22 |
| 3,153,094 | 10/1964 | Reilly | 260/576 |
| 3,826,832 | 7/1974 | Anderson et al. | 424/250 |
| 4,265,714 | 5/1981 | Nolan et al. | 204/17 |
| 4,482,533 | 11/1984 | Keith | 421/28 |
| 4,638,079 | 1/1987 | Inskip et al. | 560/4 |
| 4,708,854 | 11/1987 | Grinstead | 423/235 |
| 4,921,683 | 5/1990 | Bedell | 423/235 |
| 4,952,289 | 8/1990 | Ciccone et al. | 204/129 |
| 4,954,526 | 9/1990 | Keefer | 514/499 |
| 4,985,471 | 1/1991 | Ohta et al. | 522/27 |
| 5,039,705 | 8/1991 | Keefer et al. | 514/611 |
| 5,087,631 | 2/1992 | Shaffer et al. | 514/342 |
| 5,087,671 | 2/1992 | Loeppky et al. | 525/328.2 |
| 5,094,815 | 3/1992 | Conboy et al. | 422/52 |
| 5,155,137 | 10/1992 | Keefer et al. | 514/611 |
| 5,212,204 | 5/1993 | Keefer et al. | 514/647 |
| 5,234,956 | 8/1993 | Lipton | 514/724 |

FOREIGN PATENT DOCUMENTS

| | | |
|---|---|---|
| 425154 | 10/1990 | European Pat. Off. |
| 211789 | 7/1984 | Germany . |
| 43 05 881 | 3/1994 | Germany . |
| WO 89/12627 | 6/1989 | WIPO . |
| WO 90/09785 | 9/1990 | WIPO . |
| WO 91/04022 | 4/1991 | WIPO . |
| WO 91/05551 | 5/1991 | WIPO . |
| WO 92/05149 | 4/1992 | WIPO . |
| WO 93/07114 | 4/1993 | WIPO . |
| WO 93/20088 | 10/1993 | WIPO . |

OTHER PUBLICATIONS

Adams et al., "Electron–Affinic Sensitization," *Radiation Research*, 67, 9–20 (1976).

Alston et al., "Generation of Nitric Oxide by Enzymatic Oxidation of N–Hydroxy–N–Nitrosamines," *J. Biol. Chem.*, 260 (7), 4069–4074 (1985).

Ames et al., "Uric Acid Provides An Antioxidant Defense in Humans Against Oxidant–And Radical–Caused Aging and Cancer: A Hypothesis," *Proc. Natl. Acad. Sci. USA*, 78, 6858–6862 (1981).

Andrade et al., "Inhibitors of Nitric Oxide Synthase Selectively Reduce Flow in Tumour–Associated Neovasculature," *Br. J. Pharmacol.*, 107, 1092–1095 (1992).

Andrews et al., "Protection Against Gastric Reperfusion Injury by Nitric Oxide: Role of Polymorhophonuclear Leukocytes," *Gastroenterology*, 104, A33 (1993).

Aoki et al., "Beneficial Effects of Two forms of NO Administration in Feline Splanchnic Artery Occlusion Shock," *Am. J. Physiol.*, 258, G275–G281 (1990).

Artysbasheva et al., "Synthesis of 1–Alkoxy–3,3–Dialkyltriazene 2–Oxides from Alkoxyamines and Nitrosoamines," translated from *Zhurnal Organicheskoi Khimii* (J. Organic Chemistry–U.S.S.R.), 28, (6) 1168–1173 (1987).

Beckman et al., "Apparent Hydroxyl Radical Production by Peroxynitrite: Implications for Endothelial Injury From Nitric Oxide and Superoxide," *Proc. Natl. Acad. Sci. USA*, 87, 1620–1624 (1990).

Beckman, "The Double–Edged Role of Nitric Oxide in Brain Function and Superoxide–Mediated Injury," *J. Developmental Physiol.*, 15, 53–59 (1991).

Beckman, "Ischaemic Injury Mediator," *Nature*, 345, 27–28 (1990).

(List continued on next page.)

*Primary Examiner*—Shailendra Kumar
*Attorney, Agent, or Firm*—Leydig, Voit & Mayer, Ltd.

[57] ABSTRACT

There are disclosed N-substituted piperazine NONOate compounds having the structure:

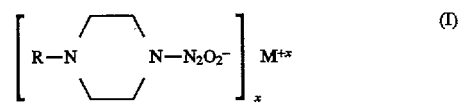

wherein M is a pharmaceutically acceptable cation, x is the valence of the cation, and R is selected from the group consisting of: an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, a group of formula,

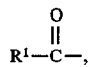

a group of formula,

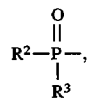

a group of formula $R^4$—$SO_2$—, or a group of formula $R^5$—O—N=N(O)—. The compounds are potent nitric oxide releasing compounds.

6 Claims, No Drawings

OTHER PUBLICATIONS

Bedford et al., "Threshold Hypoxia: Its Effect on the Survival of Mammalian Cells Irradiated at High and Low Dose–Rates," *Br. J. Radiol.*, 39, 896–900 (1966).

Bohn et al., "Oxygen and Oxidation Promote the Release of Nitric Oxide from Syndnonimines," *J. Cardiovasc. Pharmacol.*, 14, s6–s12 (1989).

Bonakdar et al., "Continous–Flow Performance of Carbon Electrodes Modified With Immobilized Fe(II)/Fe(III) Centers," *Calanta*, 36, 219–225 (1989).

Coleman et al., "Phase I Trial of the Hypoxic Cell Radiosensitizer SR–2508: The Results of the Five to Six Week Drug Schedule," *Int. J. Radiat. Oncol. Biol. Phys.*, 12, 1105–1108 (1986).

Dawson et al., "Nitric Oxide Synthase and Neuronal NADPH Diaphorase Are Identical in Brain and Peripheral Tissues," *Proc. Natl. Acad. Sci. USA*, 88, 7797–7801 (1991).

DeFeudis, "Endothelium–Dependent Vasorelaxation –A New Basis for Developing Cardiovascular Drugs," *Drugs of today*, 24 (2), 103–115 (1988).

DeGraff et al., "Evaluation of Nitroimidazole Hypoxic Cell Radiosensitizers in a Human Tumor Cell Line High in Intracellular Glutathione," *I. J. Radiation Oncology Biol. Phys.*, 16, 1021–1024 (1989).

DeLuca et al., "Parenteral Drug–Delivery Systems," in *Pharmaceutics and Pharmacy Practice* (Banker et al., eds.), 238–250 (J.B. Lippincott Co., Philadelphia, PA) (1982).

Drago et al., "The Reaction of Nitrogen(II) Oxide with Various Primary and Secondary Amines," *J. Am. Chem. Soc.*, 83, 1819–1822 (1961).

Drago, "Reactions of Nitrogen(II) Oxide," in *Free Radicals in Organic Chemistry*, Advances in Chemistry Series No. 36, 143–149 (American Chemical Society, Washington, DC) (1962).

Fast et al., "Nitric Oxide Production by Tumor Targets in Response to TNF: Paradoxical Correlation With Susceptibility to TNF–Mediated Cytotoxicity Without Direct Involvement in the Cytotoxic Mechanism," *J. Leukocyte Biol.*, 52, 255–261 (1992).

Feelisch et al., "On the Mechanism of NO Release from Sydnonimines," *J. Cardiovasc. Pharmacol.*, 14, S13–S22 (1989).

Feelisch, "The Biochemical Pathways of Nitric Oxide Formation from Nitrovasodilators: Appropriate Choice of Exogenous NO Donors and Aspects of Preparation and Handling of Aqueous NO Solutions," *J. Cardiovasc. Pharmacol.*, 17, S25–S33 (1991).

Filep et al., "Nitric Oxide Modulates Vascular Permeability in the Rat Coronary Circulation," *Br. J. Pharmacol.*, 108, 323–326 (1993).

Fujitsuka et al., "Nitrosohydroxylamines," *Chem. Abstracts*, 82, 31108P (1975).

Furchgott, "The Role of Endothelium in the Responses of Vascular Smooth Muscle to Drugs," *Ann. Rev. Pharmacol. Toxicol.*, 24, 175–97 (1984).

Gambassi et al., "Ischemia–Reperfusion Injury and Histamine Release in Isolated Perfused Guinea–Pig Heart: Effects of Nitric Oxide Generators," *Pharmacological Research*, 25, 11–12 (1992).

Garg et al., "Nitric Oxide–Generating Vasodilators Inhibit Mitogenesis and Proliferation of Balb/c3T3 Fibroblasts By A Cylic GMP–Independent Mechanism," *Biochem. and Biophys. Res. Comm.*, 171, 474–479 (1990).

Gatenby et al., "Oxygen Distribution in Squamous Cell Carcinoma Metastases and its Relationship to Outcome of Radiation Therapy," *I. J. Radiation Oncology Biol. Phys.*, 14, 831–838 (1988).

Gehlen et al., "Über Reaktionen und Eigenschaften des Stickoxyds und seiner Verbindungen (II.Mitteil): Zur Kenntnis der Salze der Stickoxyd–schwefligen Säure," *Berichte d. D. Chem, Gesellschaft*, LXV, 1130–1140 (1932). (Reactions and properties of nitric oxide and its compounds. II. The salts of the nitric oxide compound of sulfurous acid, *Chemical Abstracts*, 26, 4764–65.)

Gelvan et al., "Cardiac Reperfusion Damage Prevented by a Nitroxide Free Radical," *Proc. Natl. Acad. Sci. USA*, 88, 4680–4684 (1991).

Granger, "Role of Xanthine Oxidase and Granulocytes in Ischemia–Reperfusion Injury," *Am. J. Physiol.*, 255, H1269–H1275 (1988).

Hall, "The Oxygen Effect and Reoxygenation," in *Radiobiology for the Radiologist* (4th ed.), 133–164 (J.P. Lippincott Co., Philadelphia) (1994).

Hall et al., "Extreme Hypoxia; Its Effect on the Survival of Mamalian Cells Irradiated at High and Low Dose–Rates," *Br. J. Radiol.*, 39, 302–307 (1966).

Halliwell et al., "Oxygen Toxicity, Oxygen Radicals, Transition Metals and Disease," *Biochem. J.*, 219, 1–14 (1984).

Halliwell et al., "Biologically Relevant Metal Ion–Dependent Hydroxyl Radical Generation," *FEBS*, 307, 108–112 (1992).

Halliwell et al., "Oxygen Free Radicals and Iron in Relation to Biology and Medicine: Some Problems and Concepts," *Arch. Biochem. and Biophys.*, 246, 501–514 (1986).

Hanbauer et al., "Role of Nitric Oxide in NMDA–Evoked Release of [$^3$H]–Dopamine From Striatal Slices," *Neuroreport*, 3, 409–412 (1992).

Hansen et al., "N–Nitrosation of Secondary Amines by Nitric Oxide via the 'Drago Complex'," in *N–Nitroso Compounds: Occurrence and Biological Effects*, IARC Scientific Publications No. 41, 21–29 (International Agency for Research on Cancer, Lyon, France) (1982).

Hibbs et al., "Nitric Oxide: A Cytotoxic Activated Macrophage Effector Molecule," *Biochem. and Biophys. Res. Comm.*, 157, 87–94 (1988).

Holford et al., "Understanding the Dose–Effect Relationship: Clinical Application of Pharmacokinetic–Pharmacodynamic Models," *Clinical Pharmacokinetics*, 6, 429–453 (1981).

Howard–Flanders, "Effect of Nitric Oxide on the Radiosensitivity of Bacteria," *Nature*, 180, 1991–1192 (1957).

Hrabie et al., "New Nitric Oxide–Releasing Zwitterions Derived from Polyamines," *J. Org. Chem.*, 58, 1472–1476 (1993).

Hutcheson et al., "Role of Nitric Oxide in Maintaining Vascular Integrity in Endotoxin–Induced Acute Intestinal Damage in the Rat," *Br. J. Pharmacol.*, 101, 815–820 (1990).

Ignarro et al., "Mechanism of Vascular Smooth Muscle Relaxation by Organic Nitrates, Nitrites, Nitroprusside and Nitric Oxide: Evidence for the Involvement of S–Nitrosothiols as Active Intermediates," *J. Pharmacol. Exp. Ther.*, 218, 739–749 (1981).

Ignarro, "Endothelium–derived nitric oxide: actions and properties," *The FASEB Journal*, 3, 31–36 (1989).

Ignarro, "Biosynthesis and Metabolism of Endothelium–Derived Nitric Oxide," *Ann. Rev. Pharmacol. Toxicol.*, 30, 535–60 (1990).

Ignarro et al., "The Pharmacological and Physiological Role of Cyclic GMP in Vascular Smooth Muscle Relaxation," *Ann. Rev. Pharmacol. Toxicol.*, 25, 171–191 (1985).

Ignarro, "Nitric Oxide: A Novel Signal Transduction Mechanism for Transcellular Communication," *Hypertension*, 16, 477–483 (1990).

Imlay et al., "Toxic DNA Damage by Hydrogen Peroxide Through the Fenton Reaction in vivo and in vitro," *Science*, 240, 640–642 (1988).

Ischiropoulos et al., "Peroxynitrite–Mediated Tyrosine Nitration Catalyzed by Superoxide Dismutase," *Arch. Biochem. and Biophys.*, 298, 431–437 (1992).

Jaeschke et al., "Role of Nitric Oxide in the Oxidant Stress During Ischemia/Reperfusion Injury of the Liver," *Life Sciences*, 50, 1797–1804 (1992).

Johnson et al., "Cardioprotective Effects of Authentic Nitric Oxide in Myocardial Ischemia With Reperfusion," *Critical Care Medicine*, 19, 244–252 (1991).

Jones, "Metastable Polymers of the Nitrogen Oxides. 1. Open Chain Nitric Oxide Analogues of Polythlazyl: A MNDO/AM1 Study," *J. Phys. Chem.*, 95, 2588–2595 (1991).

Kanner et al., "Nitric Oxide as an Antioxidant," *Archives of Biochemistry and Biophysics*, 289, 130–136 (1991).

Keefer et al., "Complexes of Nitric Oxide with Nucleophiles as Agents for the Controlled Biological Release of Nitric Oxide," *Biology of Nitric Oxide, 2, Enzymology, Biochemistry, Immunology*, (Moncada et al., eds.), 153–156 (Portland Press, Chapel Hill, NC) (1992).

Kiedrowski et al., "Sodium Nitroprusside Inhibits N–Methyl–D–aspartate–Evoked Calcium Influx via a Nitric Oxide—and cGMP–Independent Mechanism," *Molecular Pharmacology*, 41, 779–784 (1992).

Kruszyna et al., "Red Blood Cells Generate Nitric Oxide from Directly Acting, Nitrogenous Vasodilators," *Toxicol. Appl. Pharmacol.*, 91, 429–438 (1987).

Kubes et al., "Nitric Oxide Modulates Microvascular Permeability," *Am. J. Physiol.*, 262, H611–H615 (1992).

Kubes et al., "Nitric Oxide: An endogenous Modulator of Leukocyte Adhesion," *Proc. Natl. Acad. Sci. USA*, 88, 4651–4655 (1991).

Kubes et al., "Nitric Oxide Protects Against Ischemia/Reperfusion–Induced Mucosal Dysfunction," *Gastroenterology*, 104, A728 (1993).

Kuhn et al., "Endothelium–Dependent Vasodilation in Human Epicardial Coronary Arteries: Effect of Prolonged Exposure to Glycerol Trinitrate or SIN–1, " *J. Cardiovasc. Pharmacol.*, 14, (Suppl. 11), S47–S54 (1989).

Kuznetsov et al., "Photoelectron spectra and electronic structures of 2–alkoxy–1–tert–alkydiazen–1–oxides and 1–alkoxy–3,3–dialkyltriazen–2–oxides," *J. Mol. Struct.*, 263, 329–341 (1991).

Kwon et al., "Inhibition of Tumor Cell Ribonucleotide Reductase by Macrophage–Derived Nitric Oxide," *J. Exp. Med.*, 174 (4) 761–767 (1991).

Lafon–Cazal et al., "NMDA–Dependent Superoxide Production and Neurotoxicity," *Nature*, 364, 535–537 (1993).

Lefer et al., "Pharmacology of the Endothelium in Ischemia–Reperfusion and Circulatory Shock," *Ann. Rev. Pharmacol. Toxicol.*, 33, 71–90 (1993).

Linz et al., "ACE–Inhibition Induces NO–Formation in Cultured Bovine Endothelial Cells and Protects Isolated Ischemic Rat Hearts," *J. Mol. Cell Cardiol.*, 24, 909–919 (1992).

Lipton et al., "A Redox–Based Mechanism for the Neuroprotective and Neurodestructive Effects of Nitric Oxide and Related Nitroso–Compounds," *Nature*, 364, 626–631 (1993).

Longhi et al., "Metal–Containing Compounds of the Anion $(C_2H_5)_2NN_2O_2$," *Inorg. Chem.*, 2, 85–88 (1963).

Lutz et al., "Isolation of Trioxodinitrato(II) Complexes of Some First Row Transition Metal Ions," *J.C.S. Chem. Comm.*, 247 (1977).

Maragos et al., "Complexes of NO with Nucleophiles as Agents for the Controlled Biological Release of Nitric Oxide. Vasorelaxant Effects," *J. Med. Chem.*, 34, 3242–3247 (1991).

Maragos et al., "Nitric Oxide/Nucleophile Complexes Inhibit the in vitro Proliferation of A375 Melanoma Cells via Nitric Oxide Release," *Cancer Res.*, 53 (3), 564–568 (1993).

Marletta et al., "Unraveling the Biological Significance of Nitric Oxide," *BioFactors*, 2, 219–225 (1990).

Marmo et al., "Cardiovascular and Respiratory Effects of Spermidine and Spermine: An Experimental Study," *Biomed. Biochim. Acta*, 43, 509–515 (1984).

Masini et al., "Effect of Nitric Oxide Generators on Ischemia–Reperfusion Injury and Histamine Release in Isolated Perfused Guinea Pig Heart," *Int. Arch., Allergy Appl. Immuno.*, 94, 257–258 (1991).

Masini et al., "The Effect of Nitric Oxide Generators on Ischemia Reperfusion Injury and Histamine Release in Isolated Perfused Guinea–Pig Heart," *Agents and Actions*, 33, 53–56 (1991).

Middleton et al., "Further Studies on the Interaction of Nitric Oxide With Transition–Metal Alkyls," *J. Chem. Soc. Dalton*, 1898–1905 (1981).

Minotti et al., "The Requirment for Iron (III) in the Initiation of Lipid Peroxidation by Iron (II) and Hydrogen Peroxide," *J. Biol. Chem.*, 262, 1098–1004 (1987).

Mitchell et al., "Biologically Active Metal–Independent Superoxide Dismutase Mimics," *Biochemistry*, 29, 2802–2807 (1990).

Mitchell et al., "Cellular Glutathione Depletion by Diethyl Maleate or Buthionine Sulfoximine: No Effect of Glutathione Depletion on the Oxygen Enhancement Ratio," *Radiation Research*, 96, 422–428 (1983).

Morikawa et al., "L–Arginine Decreases Infarct Size Caused by Middle Cerebral Arterial Occlusion in SHR," *Am. J. Physiol.*, 263, H1632–H1635 (1992).

Morley et al., "Mechanism of Vascular Relaxation Induced by the Nitric Oxide (NO)/Nucleophile Complexes, a New Class of NO–Based Vasodilators," *J. Cardiovasc. Pharmacol.*, 21, 670–676 (1993).

Murad et al., *Propr. Clin. Biol. Res.*, 249, 65–76 (1983).

Murayama et al., "Radiosensitization of Hypoxic HeLa S3 Cells in vitro by a New Type of Radiosensitizer: Spermine and Spermidine Amides with Nitro Groups," *Int. J. Radiat. Biol.*, 44, 497–503 (1983).

Myers et al., "Vasorelaxant properties of the endothelium–derived relaxing factor more closely resemble S–nitrosocystein than nitric oxide," *Nature*, 345, 161–163 (1990).

Palmer et al., "Nitric oxide release accounts for the biological activity of endothelium–derived relaxing factor," *Nature*, 327, 324–327 (1987).

Park et al., "Controlled Protein Release from Polyethyleneimine–Coated Poly(L–lactic Acid)/Pluronic Blend Matrices," *Pharmaceut. Res.*, 9, 37–39 (1992).

Phillips et al., "Variation in Sensitizing Efficiency for SR 2508 In Human Cells Dependent on Glutathione Content," *I.J. Radiation Oncology Biol. Phys.*, 12, 1627–1635 (1986).

Phillips et al., "Promise of Radiosensitizers and Radioprotectors in the Treatment of Human Cancer," *Cancer Treatment Reports*, 68, 291–302 (1984).

Powers et al., "A Multicomponent X–Ray Survival Curve for Mouse Lymphosarcoma Cells Irradiated in vivo," *Nature*, 197, 710–711 (1963).

Radi et al., "Peroxynitrite–Induced Membrane Lipid Peroxidation: The Cytotoxic Potential of Superoxide and Nitric Oxide," *Arch. Biochem. and Biophys.*, 288, 481–487 (1991).

Radomski et al., "Endogenous Nitric Oxide Inhibits Human Platelet Adhesion to Vascular Endothelium," *The Lancet*, 1057–1058 (1987).

Rapoport et al., *Protein Phosph. Research*, S (4–5), 281–296 (1983).

Rubanyi et al., "Cytoprotective Function of Nitric Oxide: Inactivation of Superoxide Radicals Produced by Human Leukocytes," *Biochem. and Biophys. Res. Comm.* 181, 1392–1397 (1991).

Russo et al., "The Effects of Cellular Glutathione Elevation on the Oxygen Enhancement Ratio," *Radiation Research*, 103, 232–239 (1985).

Saavedra et al., "Secondary Amine/Nitric Oxide Complex Ions, $R_2N[N(O)NO]$ O–Functionalized Chemistry," *J. Org. Chem.*, 57, 6134–6138 (1992).

Saran et al., "Reaction of NO With $O_2-$. Implications for the Action of Endothelium–Derived Relaxing Factor (EDRF)," *Free Rad. Res. Comm.*, 10, 221–226 (1990).

Siegfried et al., "Beneficial effects of SPM–5185, a cysteine–containing NO donor in myocardial ischemia–reperfusion," *Am. J. Physiol.*, 263, H771–H777 (1992).

Siegfried et al., "Cardioprotection and Attenuation of Endothelial Dysfunction by Organic Nitric Oxide Donors in Myocardial Ischemia–Reperfusion," *J. Pharmacol. and Exp. Therapeutics*, 260, 668–675 (1992).

Siemann et al., "Characterization of Radiation Resistant Hypoxic Cell Subpopulations In KHT Sarcomas. (ii) Cell Sorting," *Br. J. Cancer*, 58, 296–300 (1988).

Smith et al., "Nitroprusside: A Potpourri of Biologically Reactive Intermediates," in *Advances in Experimental Medicine and Biology*, 283, *Biological Reactive Intermediates IV* (Witmer et al., eds.), 365–369 (Plenum Press, New York, NY) (1991).

Smith et al., "Complex Contractile Patterns in Canine Colon Produced by Spontaneous of Nitric Oxide," *Gastroenterology*, 102 (Part 2), A516 (1992).

Stamler et al., "S–Nitrosylation of proteins with nitric oxide: Synthesis and characterization of biologically active compounds," *Proc. Natl. Acad. Sci. USA*, 89, 444–448 (1992).

Stamler et al., "Nitric Oxide Circulates in Mammalian Plasma Primarily as an S–Nitroso Adduct of Serum Albumin," *Proc. Natl. Acad. Sci. USA*, 89, 7674–7677 (1992).

Stuehr et al., "Nitric Oxide: A Macrophage Product Responsible for Cytostasis and Respiratory Inhibition in Tumor Target Cells," *J. Exp. Med.*, 169, 1543–1555 (1989).

Thomlinson et al., "The Histological Structure of Some Human Lung Cancers and the Possible Implications for Radiotherapy," *Br. J. Cancer*, IX, 539–549 (1955).

Trissel, "Intravenous Infusion Solutions," *Handbook on Injectable Drugs* (4th ed.), 622–629 (American Society of Hospital Pharmacists, Bethesda, MD) (1986).

von Sonntag, *The Chemical Basis of Radiation Biology*, pp. 31–56 and 295–352 (Taylor & Francis, London) (1987).

Weitz et al., "Zur Kenntnis der stickoxyd–schwefligen Säure (II.Mitteil)," *Berichte d. D. Chem. Gesellschaft*, LXVI, 1718–1727 (1933). (Nitrosylsulfuric acid, *Chemical Abstracts*, 28, 2636.)

WHO Task Group on Environmental Health Criteria for Oxides of Nitrogen, *Environmental Health Criteria* 4: *Oxides of Nitrogen*, (World Health Organization, Geneva) (1977).

Wiersdorff et al., "N–aryl–N–nitrosohydroxylamine salts," *Chem. Abstract*, 77, 48034f (1972).

Wilcox et al., "Effect of Cyanide on the Reaction of Nitroprusside with Hemoglobin: Relevance to Cyanide Interference With the Biological Activity of Nitroprusside," *Chem. Res. Toxicol.*, 3, 71–76 (1990).

Wink et al., "DNA Deaminating Ability and Genotoxicity of Nitric Oxide and Its Progenitors," *Science*, 254, 1001–1003 (1991).

Woditsch et al., "Prostacyclin Rather Than Endogenous Nitric Oxide is a Tissue Protective Factor in Myocardial Ischemia," *Am. J. Physiol.*, 263, H1390–H1396 (1992).

Wood et al., "Modification of Energy Metabolism and Radiation Response of A Murine Tumour by Changes in Nitric Oxide Availability," *Biochem. and Biophys. Res. Comm.*, 192, 505–510 (1993).

Zhu et al., "Bactericidal Activity of Peroxynitrite," *Arch. of Biochem. and Biophy.*, 298, 452–457 (1992).

N-SUBSTITUTED PIPERAZINE NONOATES

RELATED APPLICATIONS

The present application is a continuation-in-part of U.S. patent application Ser. No. 08/017,270, filed Feb. 12, 1993, which, in turn, is a divisional of U.S. application Ser. No. 07/743,892 filed Aug. 12, 1991 (now U.S. Pat. No. 5,208,233) which, in turn, is a continuation-in-part of U.S. application Ser. No. 07/409,552 filed Sep. 15, 1989 (now U.S. Pat. No. 5,039,705), each of which are expressly incorporated herein by reference in their entirety. The present application is also a continuation-in-part of U.S. patent application Ser. No. 07/950,637, filed Sep. 23, 1992, now U.S. Pat. No. 5,366,997, which is a continuation-in-part of U.S. application Ser. No. 07/764,908, filed Sep. 24, 1991, now abandoned.

TECHNICAL FIELD OF THE INVENTION

The present invention relates to novel N-substituted piperazine NONOate compounds. In particular, the present invention relates to N-substituted piperazine compounds, bearing substituents such as acyl, sulfonyl, phosphoryl, alkyl, alkenyl, or the like and derivatives thereof to which are bound nitric oxide-releasing $N_2O_2^-$.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175–197, 1984.) Recently, Palmer et al., have shown that EDRF is identical to the simple molecule, nitric oxide, NO (Nature 317j 524–526, 1987) . It has been hypothesized for years that many nitrovasodilators that mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox. & Appl. Pharmacol., 91, 429–438, 1987; Ignarro, FASEB J. 3, 31–36, 1989 and Ignarro et al., J. Pharmacol. Exper. Therapeutics 218(3), 739–749, 1981.)

BRIEF SUMMARY OF THE INVENTION

It has now been discovered that certain N-substituted piperazine NONOate compounds, having the structure:

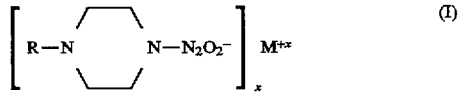
(I)

wherein M is a pharmaceutically acceptable cation, x is the valence of the cation, and R is selected from the group consisting of: an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, a group of formula

a group of formula,

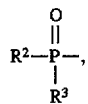

a group of formula $R^4$—$SO_2$—, or a group of formula $R^5$—O—N=N(O)—, are potent nitric oxide releasing compounds. Nitric oxide releasing compounds, among other aspects, act as vasodilatory anti-hypertensives and thus are useful for treating cardiovascular disorders in which lowering the blood pressure has a beneficial result. It is believed that such nitric oxide releasing compounds function by releasing NO in the blood after injection; however the invention should not be limited by this hypothesis. In addition to having potent nitric oxide releasing capabilities, the N-substituted piperazine NONOates are effective at tagging polypeptides and proteins, thus creating potent NO releasing proteins.

DETAILED DESCRIPTION OF THE INVENTION

The present invention provides N-substituted piperazine NONOate compounds, having the structure:

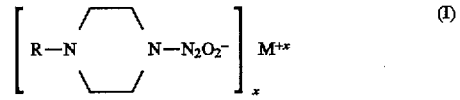
(I)

wherein M is a pharmaceutically acceptable cation, x is the valence of the cation, and R is selected from the group consisting of: an unsubstituted or substituted $C_1$–$C_{20}$ straight chain alkyl, an unsubstituted or substituted $C_3$–$C_{20}$ branched chain alkyl,an unsubstituted or substituted $C_2$–$C_{20}$ straight chain alkenyl, an unsubstituted or substituted $C_3$–$C_{20}$ branched chain alkenyl, a group of formula

a group of formula,

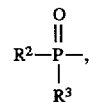

a group of formula $R^4$—$SO_2$—, or a group of formula $R^5$—O—N=N(O)—.

$R^1$ may be any of hydrogen, alkyl, substituted alkyl, alkenyl, substituted alkenyl, aryl, substituted aryl, heteroaryl, alkylthio, arylthio, alkoxy, aryloxy, amino, a mono- or di-substituted amino, and succinimidoxy.

$R^2$ and $R^3$ may be the same or different and may be any of aryl, substituted aryl, heteroaryl, alkylthio, arylthio, mercapto, hydroxy, alkoxy, halo, aryloxy, amino, a mono- or di-substituted amino, phosphate, a mono- or di-substituted phosphate, an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, and an unsubstituted or substituted $C_3$–$C_{20}$ branched chain alkenyl.

$R^4$ may be any of an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, aryl, substituted aryl, and heteroaryl.

$R^5$ may be any of an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, and a noncovalently bound cation.

The substituted $C_1$–$C_{20}$ straight chain alkyl may be substituted with one or more substituents selected from the group consisting of: aryl, substituted aryl, heteroaromatic aryl, alkylthio, arylthio, acylthio, mercapto, hydroxy, aryloxy, alkoxy, halo, carboxy and esters thereof, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

The substituted $C_3$–$C_{20}$ branched chain alkyl may be substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

The substituted $C_2$–$C_{20}$ straight chain alkenyl may be substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

The substituted $C_3$–$C_{20}$ branched chain alkenyl may be substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

Any of $R^1$, $R^2$, $R^3$, $R^4$ and $R^5$ may be substituted with a $C_1$–$C_{20}$ straight chain alkyl, a substituted $C_3$–$C_{20}$ branched chain alkyl, a substituted $C_2$–$C_{20}$ straight chain alkenyl, or a substituted $C_3$–$C_{20}$ branched chain alkenyl, with or without one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono-or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, and acyloxy.

By a pharmaceutically acceptable cation is meant any non-toxic cation; these are well known to one of ordinary skill in the art. The cation should not render the compound unstable or insoluble in water. Generally, the cation will be a group 1 or group 2 cation, such as sodium, potassium, magnesium or calcium ions. The most preferred cations are $Na^+$, $K^+$, $Ca^{+2}$, and $Mg^{+2}$.

The disclosed compounds are potent nitric oxide releasing compounds. Nitric oxide releasing compounds, among other aspects, act as vasodilators and anti-hypertensives and thus are useful for treating cardiovascular disorders in which lowering the blood pressure has a beneficial result. It is believed that such nitric oxide releasing compounds function by releasing NO in the blood after injection; however the invention should not be limited by this hypothesis. In addition to having potent nitric oxide releasing capabilities, the N-substituted piperazine NONOates are effective for tagging polypeptides and proteins, thus creating potent NO releasing proteins. N-substituted piperazine NONOates may be covalently attached to a polypeptide chain at either terminus or within the chain itself, such that the resulting protein has a potent NO releasing compound attached to it and may be used as an anti-hypertensive agent or any other suitable use.

The compounds of the present invention may be included in pharmaceutical compositions for administration to a mammal, including humans. The pharmaceutical compositions may comprise one or more of the compounds described herein and a suitable pharmaceutical carrier, such as those presently known to those skilled in the art.

EXAMPLES

The preparation and characterization of N-substituted piperazines containing the nitric oxid-releasing $N_2O_2^-$ functional group are illustrated in the following examples:

Example I

This example illustrates the preparation of Ethyl-1- Piperazine Carboxylate-4-Nitric Oxide Complex/Sodium salt, as shown schematically as follows:

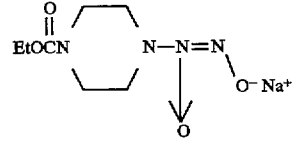

A solution of 20g (0.126 mol) of carboethoxy piperazine in 60 ml of methanol was placed in a Parr bottle. The solution was treated with 27.4 ml (0.126 mol) of 25% sodium methoxide in methanol, the system was evacuated, charged with 40 psi of nitric oxide and kept at 25° C. for 48 hr. The white crystalline product was collected by filtration and washed with cold methanol as well as with copious amounts of ether. The product was dried under vacuum to give 14.5g(48%) yield of ethyl-1 piperazine carboxylate-4-nitric oxide complex/sodium salt: mp: 184°–5° C.; uv(0.01N NaOH) λmax(ε), 252 nm (10,396); NMR ($D_2$); 1.254 (t,3H), 3.107(m,2H), 3,677(m,2H), 2.147(q,2H) . Anal calcd. for $C_6H_{13}N_4O_4Na$: C 35.00% H 5.42%, N 23.33%, Na 9.58%.

Found: C 34.87%, H 5.53%, N 23.26%, Na 9.69%. The halflife of this compound at pH 7 and 25° C. was assessed at 5 minutes. This measurement was based on the loss of the 252 nm chromophore in the ultraviolet spectrum.

Example II

This example demonstrates the attachment of a nucleophilic center to a protein that does not contain a nucleophilic center that will readily react with NO, yielding the compound 1-[4-N-acetyl-L-methionyl)piperazin-1-y]-1-oxo-2-hydroxydiazine, sodium salt shown schematically as follows:

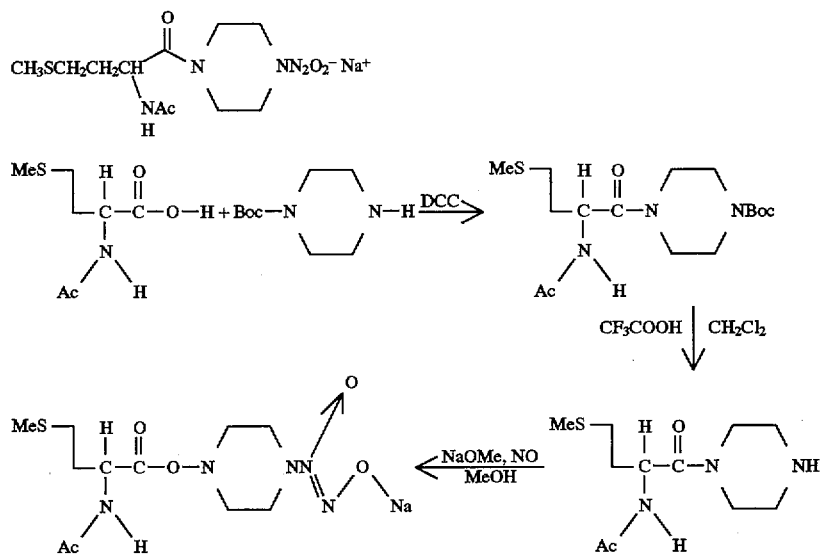

A solution of 4.78 g (0.025 mol) of N-acetyl-L-methionine in $CH_2Cl_2$: acetonitrile (120 ml) was cooled to 0° C. To this solution was added 5.36 g (0.025 mol) of dicyclohexylcarbodiimide (DCC) followed by the rapid addition of 3.90 g (0.021 mol) of N-t-butoxycarbonylpiperazine in 6 ml of dichloromethane. The progress of the reaction was followed on silica gel TLC plates developed with 4:1 acetonitrile: tetrahydrofuran and visualized with either iodine or ninhydrin spray. The reaction was complete within 2 h. A few drops of glacial acetic acid were added to the reaction mixture and the solvent was removed on a rotary evaporator. The residue was taken up in ether and filtered. The clear filtrate was washed with dilute acid followed by dilute base. The organic layer was separated, dried over anhydrous sodium sulfate, filtered, and evaporated to give 8.2 g of 1-(t-butoxycarbonyl)-4-(N-acetyl-L-methionyl)piperazine, a colorless oil which required no further purification: IR (film) 3304, 3058, 2973, 2931, 2868, 1701, 1645, 1539, 1420, 1237, 1173 $cm^{-1}$; NMR ($CDCl_3$) δ 1.47 (s, 9 H), 1.80 (m, 2 H), 2.02 (s, 3 H), 2.10 (s, 3 H), 2.46 (m, 2 H), 3.53 (m, 8 H), 5.10 (M, 1 H), 6.35 (b, 0.5 H), 6.43 (b, 0.5 H).

To a solution of 8.6 g (0.024 mol) of 1-(t-butoxycarbonyl)-4(N-acetyl-L-methionyl)piperazine in 60 ml of dichloromethane was added 10 ml of trifluoroacetic acid and the mixture was stirred at room temperature overnight. The solution was extracted with water and the resulting aqueous solution was made basic with sodium hydroxide. The product was extracted with dichloromethane, dried over sodium sulfate, and filtered. Evaporation of the solvent gave 2.1 g of 1-(N-acetyl-L-methionyl)piperazine, as an oil: IR (film) 3304, 3051, 2917, 2861, 1645, 1546, 1448, 1377 $cm^{-1}$; NMR ($CDCl_3$) δ 1.95 (m, 2 H), 2.02 (s, 3 H), 2.10 (s, 3 H), 2.54 (m, 2 H), 2.98 (m, 4 H), 3.74 (m, 4 H), 5.10 (m, 1 H), 6.40 (b, 0.5 H), 6.48 (b, 0.5 H).

To a solution of 510 mg (1.97 mmol) of 1-(N-acetyl-L-methionyl)piperazine in 1 ml of methanol was added 428 μ(1.97 mmol) of 25% sodium methoxide in methanol. The system was degassed and charged with 40 psi of nitric oxide. After exposure of the solution to NO for 120 h, the pressure was released and the solid product was collected by filtration, washed with ether, and dried to give 27 mg of 1-[4-(N-acetyl-L-methionyl)piperazin-1-yl]-1-oxo-2-hydroxydiazene, sodium salt, as a white solid: UV $\lambda_{max}$ (δ) 252 nm (12.0 $mM^{-1}$ $cm^{-1}$ ). The product decomposed with a half-life of 6.9 min at pH 7 and 25° C. to produce 1.72 moles of NO per mole of test agent.

Example III

This example illustrates the preparation of 1-Piperazine [2-methoxydiazene- 1-oxide]-4-Nitric oxide complex sodium salt, as shown schematically as follows:

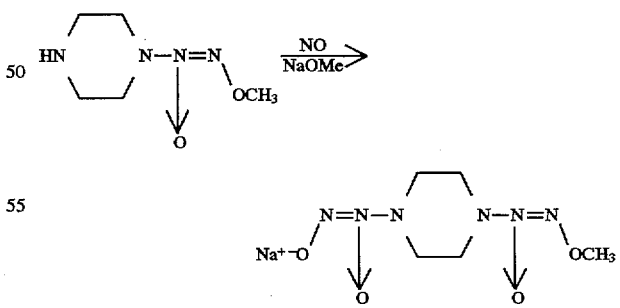

A solution of 271mg (1.69 mmol) of 1-methoxy-2-oxo-piperazyl diazene in 1 ml of methanol was placed in a micro Parr bottle and treated with 0.368 ml (1.69 mmol) of 25% sodium methoxide in methanol. The solution was flushed with nitrogen and charged with 40 psi of nitric oxide at 25° C. forming a solid mass within 24 h. The pressure was released, the solid suspended in ether and collected by filtration to give 156 mg (38%) of product: mp 165–6° C.; UV in 0.01N NaOH, λmax (ε) nm (18,984). The halflife in pH 7.4 buffer at ambient temperature was measured at 8 minutes for the ionic side, and stable for the protected side; NMR ($D_2O$), 3.327 (m,4H), 3,659 (m, 4H), 4.090 (s, 3H).

Example IV

This example illustrates the preparation of GLO/NO (Dansylpiperazine NONOate), as shown schematically as follows:

Dansylpiperazine was prepared by refluxing a solution of 7.98 g piperazine (9.27 mmol) and 5.00 g dansyl chloride (18.5 mmol) in 100 mL toluene for 6 h. The product was isolated by washing the solution with 5% NaOH and then water and concentrating in vacuo to yield 5.0 g (84%) dansylpiperazine as yellow-green powder. $^1$H NMR (200 MHz, $CDCl_3$) 2.7–2.9 (4H, multiplet), 2.9 (6H, singlet), 3.1–3.3 (4H, multiplet), 7.1–7.6 (3H, multiplet), 8.2–8.6 (3H, multiplet).

To prepare GLO NO, a solution of 3.08 g (9.64 mmol) dansylpiperazine and 2.20 mL (9.64 mmol) sodium methoxide 25% solution in methanol in 25 mL N,N-dimethylformamide was treated with NO gas at 80 psig for 2 days. After flushing with argon, 150 ML ether was added and the product isolated by filtration. Yield 2.0 g (52%) mp 158°–160° C. dec. $^1$H NMR (200 MHz, $D_2O$) 2.8 (6H, singlet), 3.1–3.2 (4H, multiplet), 3.4–3.5 94H, multiplet), 7.3–7.7 (3H, multiplet), 8.2–8.5 (3H, multiplet).

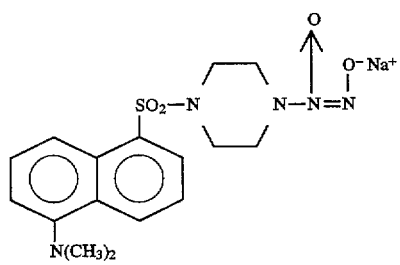

We claim:
1. An N-substituted piperazine having the formula:

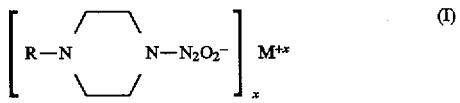

wherein M is a pharmaceutically acceptable cation, x is the valence of the cation, and R is selected from the group consisting of:
   an unsubstituted or substituted $C_1$–$C_{20}$ straight chain alkyl;
   an unsubstituted or substituted $C_3$–$C_{20}$ branched chain alkyl;
   an unsubstituted or substituted $C_2$–$C_{20}$ straight chain alkenyl;
   an unsubstituted or substituted $C_3$–$C_{20}$ branched chain alkenyl; a group of formula

wherein $R^1$ is selected from the group consisting of: hydrogen, alkyl, substituted alkyl, alkenyl, substituted alkenyl, aryl, substituted aryl, heteroaryl, alkylthio, arylthio, alkoxy, aryloxy, amino, a mono- or di-substituted amino, and succinimidoxy; a group of formula

wherein $R^2$ and $R^3$ may be the same or different and are selected from the group consisting of: aryl, substituted aryl, alkylthio, arylthio, mercapto, hydroxy, alkoxy, halo, aryloxy, amino, a mono- or di-substituted amino, phosphate, a mono- or di-substituted phosphate, an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl;
   a group of formula $R^4$—$SO_2$—, wherein $R^4$ is selected from the group consisting of: an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, aryl, substituted aryl;
   a group of formula $R^5$—O—N=N(O)—, wherein $R^5$ is selected from the group consisting of: an unsubstituted or substituted $C_1$–$C_{20}$ straight chain alkyl, an unsubstituted or substituted $C_3$–$C_{20}$ branched chain alkyl, an unsubstituted or substituted $C_2$–$C_{20}$ straight chain alkenyl, an unsubstituted or substituted $C_3$–$C_{20}$ branched chain alkenyl, a noncovalently bound cation.

2. The compound of claim 1, wherein said substituted $C_1$–$C_{20}$ straight chain alkyl is substituted with one or more substituents selected from the group consisting of: aryl, substituted aryl, heteroaromatic aryl, alkylthio, arylthio, acylthio, mercapto, hydroxy, aryloxy, alkoxy, halo, carboxy and esters thereof, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

3. The compound of claim 1, wherein said substituted $C_3$–$C_{20}$ branched chain alkyl is substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

4. The compound of claim 1, wherein said substituted $C_2$–$C_{20}$ straight chain alkenyl is substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

5. The compound of claim 1, wherein said substituted $C_3$–$C_{20}$ branched chain alkenyl is substituted with one or more substituents selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, acyloxy, with the proviso that there be no hydroxy, halo, mercapto, or phosphate substituent on the carbon attached to the piperazine ring.

6. The compound of claim 1, wherein when any of $R^1$, $R^2$, $R^3$, $R^4$ and $R^5$ is a substituted $C_1$–$C_{20}$ straight chain alkyl, a substituted $C_3$–$C_{20}$ branched chain alkyl, a substituted $C_2$–$C_{20}$ straight chain alkenyl, or a substituted $C_3$–$C_{20}$ branched chain alkenyl, said substituent(s) is (are) selected from the group consisting of: aryl, substituted aryl, heteroaryl, alkylthio, arylthio, acylthio, mercapto, hydroxy, aryloxy, alkoxy, halo, carboxy and esters thereof, amino, a mono- or di-substituted amino, phosphoryloxy, a mono- or di-substituted phosphoryloxy, phosphonyloxy, a mono- or di-substituted phosphonyloxy, phosphonyl, carbonyl, acyl, aroyl, carboxamido, cyano, nitro, oximino, and acyloxy.

* * * * *